United States Patent [19]

Durley, III et al.

[11] Patent Number: 4,902,399

[45] Date of Patent: Feb. 20, 1990

[54] FLOW-THROUGH ELECTROCHEMICAL SENSOR

[75] Inventors: Benton A. Durley, III, Antioch; Steven G. Schultz, Winthrop Harbor; Charles M. Galitz, Grayslake, all of Ill.

[73] Assignee: Abbott Laboratories, Abbott Park, Ill.

[21] Appl. No.: 337,007

[22] Filed: Apr. 12, 1989

[51] Int. Cl.$^4$ ............................................. G01N 27/28
[52] U.S. Cl. .................................... 204/409; 204/411
[58] Field of Search ................................ 204/409, 411

[56] References Cited

U.S. PATENT DOCUMENTS

| | | | |
|---|---|---|---|
| 3,997,420 | 12/1976 | Buzza | 204/411 |
| 4,206,027 | 6/1980 | Schindler et al. | 204/411 |
| 4,627,893 | 12/1986 | Cormier et al. | 204/1 T |
| 4,797,191 | 1/1989 | Metzner et al. | 204/411 |
| 4,814,282 | 3/1989 | Holen et al. | 436/165 |

Primary Examiner—G. L. Kaplan
Attorney, Agent, or Firm—Thomas D. Brainard; John W. Cornell

[57] ABSTRACT

An improved ISE is provided for measuring the concentration of an electrolyte in a sample in a centrifuge-type analyzer utilizing a multichamber test pack. The reference cell and sensor cell of the ISE are each comprised of an electrode, fill solution, housing and membrane in a fully self-contained configuration. Each cell is of sufficiently small size to fit in the test pack. The electrode of each cell is provided with screw threads to allow each cell to be screwed directly into the test pack thereby securing the cell to the test pack and at the same time providing a convenient electrical contact to the readout electronics of the test pack. With the present design manipulation of the ISE sensor output voltage can be achieved by varying the known ion concentration of the fill solution. Also provided is a novel method of introducing a fill solution into the cell after all of the cell components are in place.

17 Claims, 6 Drawing Sheets

FLOW-THROUGH ELECTROCHEMICAL SENSOR

FIELD OF THE INVENTION

This invention relates generally to an apparatus for measuring the concentrations of electrolyte components such as potassium, sodium and others in samples such as fluids. More particularly, the invention relates to a miniaturized screw-in ion selective electrode system adapted for use in a centrifugal clinical analyzer of the type that utilizes a multichamber test cartridge. In addition, the invention relates to a method of manufacture for the miniaturized ion selective electrode system.

This application is related to the following commonly-assigned applications being filed concurrently herewith: U.S. Ser. No. 336,944, relating to a REFERENCE ELECTRODE; and two continuations-in-part from U.S. Ser. No. 196,120 filed May 25, 1988, the first Ser. No. 337,011 describing a TWO PART TEST CARTRIDGE FOR CENTRIFUGE and the second Ser. No. 336,943 relating to digital electronic aspects of an APPARATUS FOR MEASURING ELECTROLYTES. The entire disclosures of each of these above-identified applications are specifically incorporated herein by reference.

BACKGROUND OF THE INVENTION

It is often necessary or desirable in determining and evaluating the condition of a patient to determine the concentration of certain electrolytes in the patient's system. Typically, the presence and concentration of electrolytes is determined by analyzing a sample of whole blood or blood serum taken from the patient. Common electrolyte components of interest include potassium, sodium, chloride, carbon dioxide, lithium, ammonium, and pH, to name a few.

Traditionally, such electrolytes have been detected and measured using flame spectrophotometric techniques. Generally, in flame spectrophotometry, a chemical composition is prepared from a sample containing the electrolyte or electrolytes of interest. The composition is then combusted and optical measurements of the resulting flame are made. The spectral characteristics of the flame are then analyzed to determine the presence and concentration of the electrolytes of interest in the sample. The value of flame spectrophotometric techniques is limited by their ability to operate on serum only and not whole blood. In addition, in flame spectrophotometry, it is critical but very difficult to precisely control the combustion of the prepared compound. Consequently, this technique is operator intensive and it is typically not possible to obtain a high degree of repeatability.

In order to overcome the drawbacks and limitations associated with traditional flame spectrophotometric techniques, ion selective electrode apparatus and measuring techniques have been developed. Ion Selective Electrodes (ISE) are devices used to generate an electrical signal (typically a potential) in proportion to the concentration of an electrolyte in a sample such as whole blood. A typical potassium sensitive ISE system is constructed of a pair of electrochemical half-cells. One half-cell, the ISE sensor, generally consists of an electrode and a membrane separated by a fill solution of known potassium concentration. The membrane has an affinity for potassium ions and is typically made from an ion-sensitive polymeric composition. When the half-cell membrane is brought in contact with a sample, the membrane forms a very specific complex with the potassium ions in the sample and, as a result of the accumulated cations, develops a potential across the membrane that is proportional to the unknown potassium concentration in the sample. This relationship closely follows the Nernst equation as is well known in the art. Therefore by knowing the ion concentration on the fill solution side of the membrane and measuring the potential across the membrane, it is possible to calculate the unknown ion concentration on the opposite side of the membrane. A second half-cell, optimized to generate a negligible potential, completes the circuit through the ISE system.

Centrifugal-type analyzers are used to perform a variety of clinical tests on a fluid sample such as whole blood. One such analyzer is fully described in the article by Schultz, et al., entitled "Two Dimensional Centrifugation for Desk Top Clinical Chemistry", Clinical Chemistry, 31/9, pp. 1457-1463 (1985). The analyzer uses centrifugal force to separate serum or plasma from whole blood and measure reagent and plasma volumes. The device is based on a two-dimensional centrifugation process in which a multi-chamber plastic test cartridge containing the sample is centrifuged at 500 times G in two planes oriented at right angles to each other.

Known ISEs are often too large and heavy to fit into the test cartridge of conventional centrifugal-type analyzers. Alternatively, they require several additional solutions for proper operation or have a mechanical configuration that prohibits user replacement.

Accordingly, it is an object of this invention to provide an ISE of sufficiently small size and configuration to allow placement of the ISE within the test cartridge of a conventional centrifugal-type analyzer. It is another object of this invention to provide such an ISE which is a self-contained system, while allowing for user replacement of ISE parts. A further object of the present invention is to provide a mechanical contact that not only holds the ISE in the test cartridge but also provides electrical connection between the ISE and the test cartridge. A further object of the present invention is to provide fill solutions and storage solutions of a composition similar to that of the sample of interest, in order to help prevent drift of the ISE generated potential, and help establish a chemical equilibrium during storage. An even further object of the present invention is to provide a miniaturized screw-in ISE for use in the multichamber test cartridge of a two-dimensional centrifugal analyzer.

SUMMARY OF THE INVENTION

To these and other ends, the invention comprises a test cartridge having a flow passage for passing a sample. The test cartridge also defines first and second socket means in communication with the passage. The communication between the socket means (first and second) and the flow passage is in the form of an open path between the socket means (first and second) and the flow passage. Cup means holds a sensor fill solution of known ion concentration, and has an open top end and a bottom end defining an orifice. A first electrode is secured to and closes the top end of the cup means, forming an electrochemical half-cell (sensor half-cell), and is removably attached to the test cartridge via the first socket means. The first socket means also provides electrical contact between the first electrode and the test cartridge. A membrane covers the orifice and is disposed between the flow passage and the cup means in order to contact the sample. A reference electrode is removably attached to the test cartridge via second socket means and also contacts the sample via the flow passage. The reference electrode is in circuit with the sensor half-cell.

The removable attachment of the sensor half-cell to the first socket means is preferably achieved by providing screw threads for screwing directly into the test cartridge, thereby securing the sensor half-cell to the test cartridge and at the same time providing a convenient electrical contact to the read-out electronics of the test cartridge. This screw-in design also allows for separate placement of the sensor half-cell and the reference electrode in the test cartridge and thereby aids in system manufacture and troubleshooting, both in the field and in research/development. Also the screw-in design allows for easy removal and replacement of worn out half-cells by the user with no special skill requirement. The fully self-contained electrode/cup (half-cell) configuration needs only sample, calibrators and readout electronics. Also the electrode/cup configuration is of sufficiently small size to fit into the test cartridge.

Another aspect, of the present invention is the use of fill solution and salt storage solution that is similar to the sample of interest, thereby minimizing drift of the potential generated by the ISE system and helping to provide chemical equilibrium during storage for prolonged life and stability.

Still another aspect of the present invention is the provision of a novel method of manufacturing the invention. The method utilizes vacuum environment to introduce the fill solution into the cup means after the electrode is secured in place.

The foregoing objects and advantages of the present invention will be further understood upon consideration of the following detailed description of the invention taken in conjunction with the accompanying drawings in which:

DETAILED DESCRIPTION OF THE INVENTION

1. Centrifugal Analyzer

The overall design and operation of the two-dimensional centrifugal analyzer used in conjunction with the present invention is generally shown in U.S. Pat. No. 4,814,282, issued on Mar. 21, 1989, and owned by the assignee of the present invention. The centrifugal analyzer is also described in the article by Schultz et al., entitled "Two Dimensional Centrifuge for Desk Top Clinical Chemistry", Clinical Chemistry 31/9 (1985). The entire disclosures of the above publications are incorporated herein by reference.

Figure 1A:
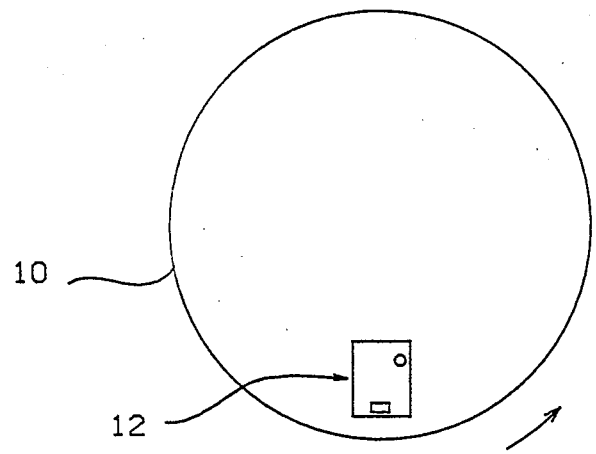
FIGS. 1a-d are schematic and elevational views of a two-dimensional centrifugal analyzer utilized in conjunction with the present invention, at various stages of rotation.
Figure 1B:
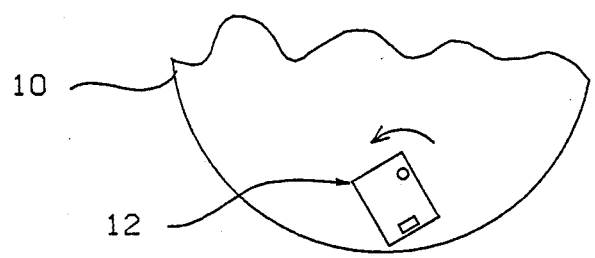
Figure 1C:
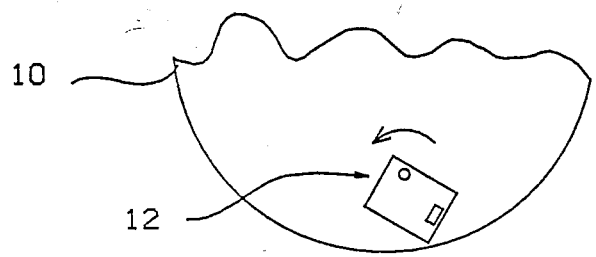
Figure 1D:
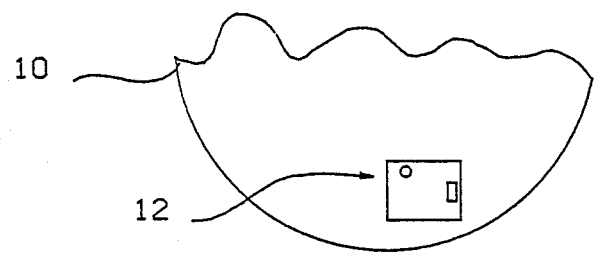

Referring now to the drawings, FIGS. 1a–1d illustrate part of the two-dimensional centrifuge operation. As seen in FIG. 1a, for example, the system generally comprises a rotatable centrifuge head 10 and a test cartridge 12. Each test cartridge 12 typically contains individual wells for holding calibration and sample fluids, and various interconnecting passages through which the fluids may be passed. The centrifuge head 10 can hold up to ten test cartridges 12 at a time and rotates at around 1800 rpm (or 500 times G). In FIGS 1b–1d, the back and forth rotation of the test cartridge 12 changes the relative G-force vectors within the test cartridge 12 and thereby manipulates the internal fluids of the test cartridge 12 throughout the various passages in order to perform chemical tests.

2. Test Cartridge

The preferred test cartridge 12 as utilized in conjunction with the present invention is fully described in previously referenced U.S. Ser. No. 337,011 entitled Two-Part Test Cartridge for Centrifuge, filed concurrently herewith and assigned to the same assignee. The entire disclosure of that application is incorporated herein by reference. The test cartridge 12 preferably has two parts, a reusable portion 70, shown in FIG. 5, and a disposable portion 96, shown in FIG. 6. Area 60 of reusable portion 70 houses the read-out electronics (not shown). The read-out electronics converts the electrical output (typically a potential difference) generated by the ISE system into an optical signal capable of being detected and read by the centrifugal analyzer. Suitable electronics for accomplishing the electrical to optical conversion is generally shown in previously referenced U.S. Ser. No. 196,120 for an Apparatus For Measuring Electrolytes, filed May 25, 1988, as well as in a continuation-in-part U.S. Ser. No. 336,943 from U.S. Ser. No. 196,120 filed concurrently herewith, and owned by the assignee of the present invention. The entire disclosures of those applications are also incorporated herein by reference. Two piercing pins 72 and 73 shown in FIG. 5 and formed in the reusable portion 70, puncture membranes in the disposable portion 96 to release calibrators A and B so that the test cartridge and analyzer may then be put into operation.

The disposable portion 96 houses the various wells and fluid paths for manipulation of the fluids during centrifugation. The reusable portion 70 and the disposable portion 96 snap together to form the single test cartridge 12 referenced in FIGS. 1a–1d.

Figure 6:
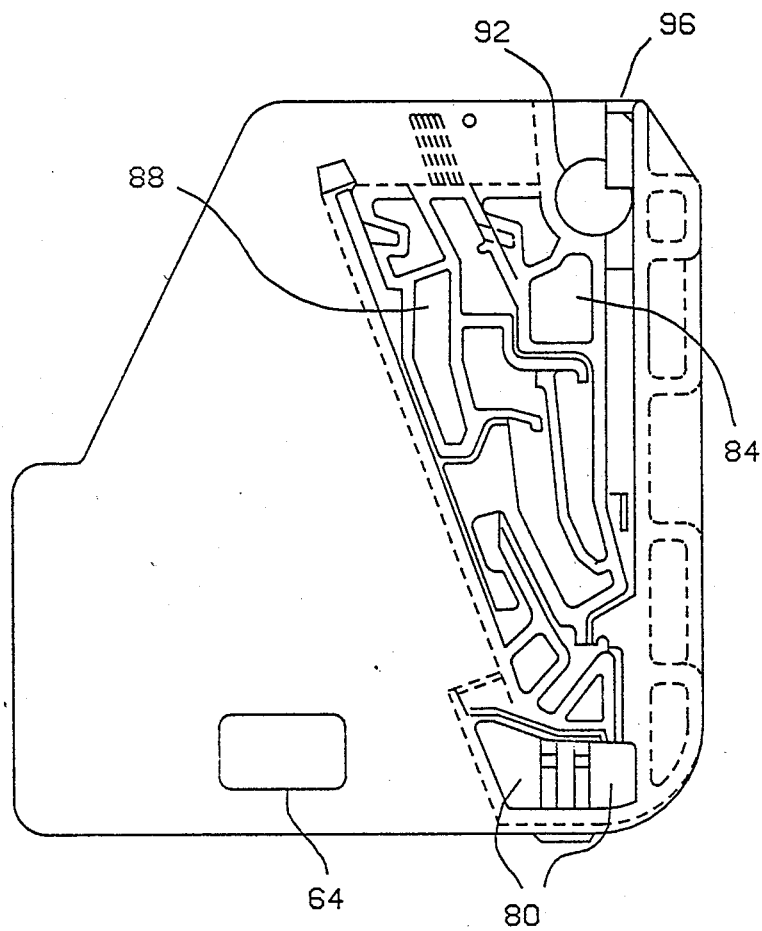
FIG. 6 is an elevational view of the disposable portion of the test cartridge illustrating the various compartments.

As shown in FIG. 6, a sample to be analyzed, such as blood, is placed in the sample well 92 of the disposable portion 96. Similarly, two calibrator fluids, designated calibrator A (or low) and calibrator B (or high), are initially placed during manufacture in wells 88 and 84, respectively. The calibration fluids are typically used in scaling the system and establishing parameters for testing the sample.

Figure 4:
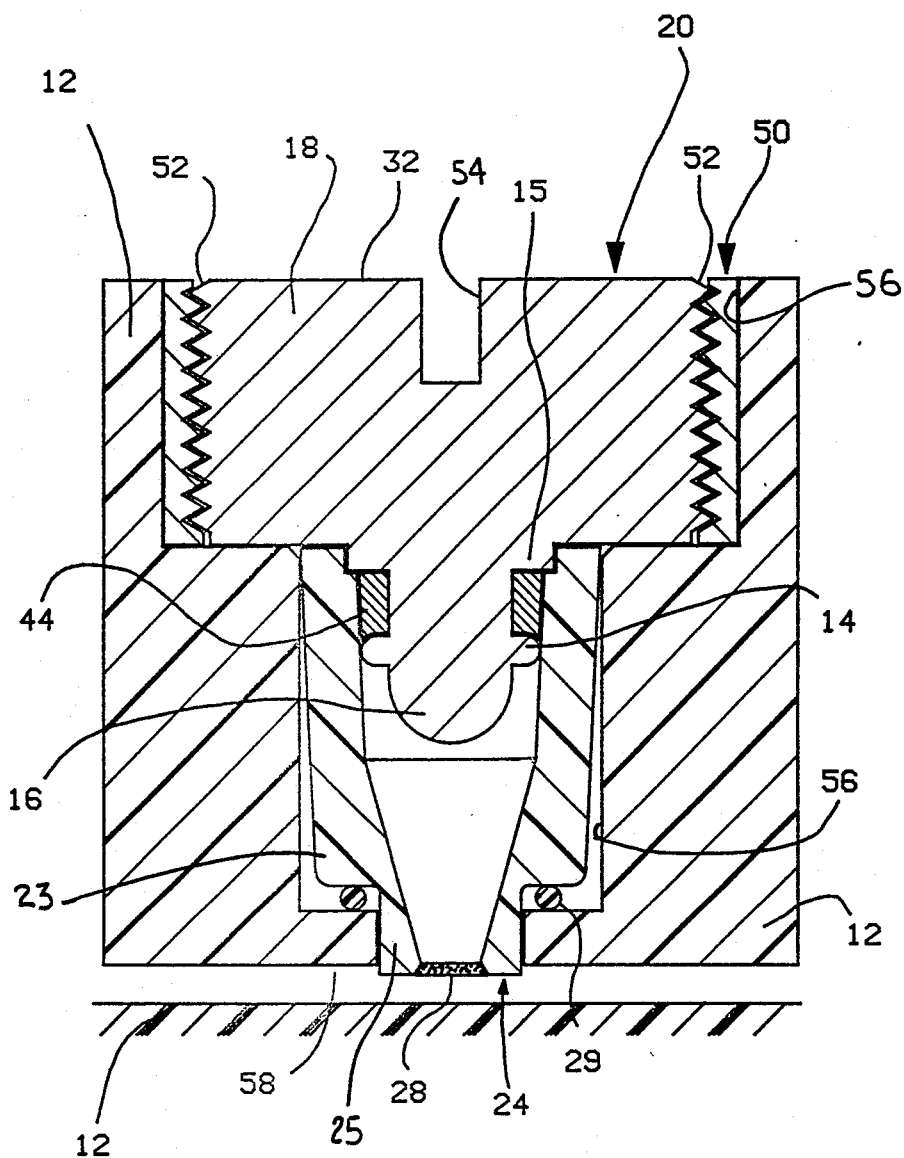
FIG. 4 is a vertical sectional view of a single electrochemical half-cell of the miniaturized screw-in ion selective electrode-system, in place in a typical test cartridge.
Figure 5:
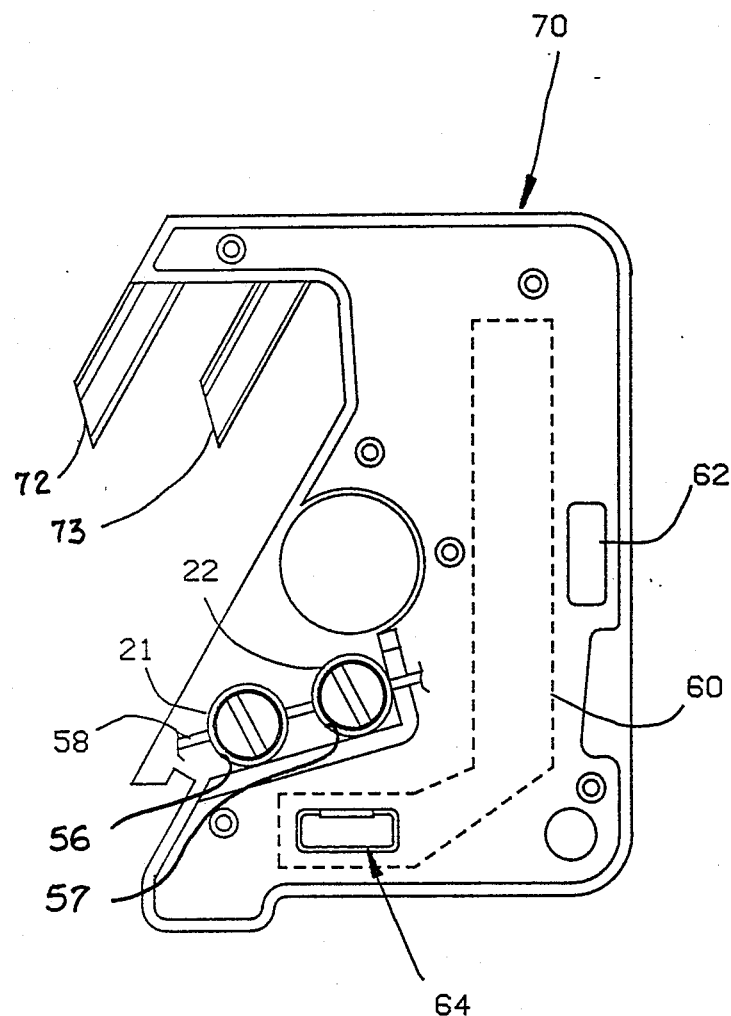
FIG. 5 is an elevational view of the reusable portion of the test cartridge with the sensor half-cell and reference half-cell of the miniaturized screw-in ion selective electrode system in place in the test cartridge.

FIG. 4 illustrates the fully assembled ISE system comprising reference and sensor half-cells 21 and 22 respectively, in position inside the test cartridge 12. Test cartridge 12 defines a substantially cylindrical first opening 56 generally conforming to the outside configuration of the half-cell 32. At the top of first opening 56 is a socket 50, preferably made of brass, and sized to engage screw threads 52 of electrode 20. The socket 50 and screw threads 52 provide electrical contact between the half-cell 32 and the read-out electronics of the test cartridge 12. The half-cell 32 screws securely into the socket 50, and thus can be easily mounted to and removed from test cartridge 12. When so mounted, a fluid path 58, formed at the bottom of opening 56 and in open communication with opening 56, brings fluid from various passages and wells of test cartridge 12 into contact with membrane 28 of half-cell 32. A second opening 57 in the test cartridge 12 has a similar reference half-cell 21 as shown in FIG. 5.

As discussed herein, half-cell 32, depending on its construction, may be used for either sensing or reference purposes, an inophore being present in the former and absent in the later. FIG. 5 illustrates the location of such half-cells 21 and 22 in test cartridge 12. Thus, the positions of the reference half-cell 21 and sensor half-cell 22 of the miniaturized screw-in ISE system are shown to be located in the reusable portion 70 of the test cartridge 12. The relationship to flow passage 58 of such half-cells 21 and 22, is shown in FIGS. 4 and 5. Area 60 of the reusable portion 70 houses the read-out electronics, including a liquid crystal display (LCD) 64, whose operation is explained in the previously referenced co-pending application U.S. Ser. No. 196,120 as well as in continuation-in-part U.S. Ser. No. 336,943 from U.S. Ser. No. 196,120 filed concurrently herewith.

FIG. 6 illustrates the disposable portion 96 of the test cartridge 12 with chamber 88 for holding calibrator A fluid, and chamber 84 for holding calibrator B fluid. Well 92 is used to hold the sample to be tested. Various passages and chambers which, among other things, interconnect the various wells and/or the fluid path 58 shown in FIG. 4, are also shown. These are described in further detail in previously referenced co-pending application U.S. Ser. No. 337,011 and such description will not be repeated here.

3. ISE Sensor Half-Cell

Figure 2B:
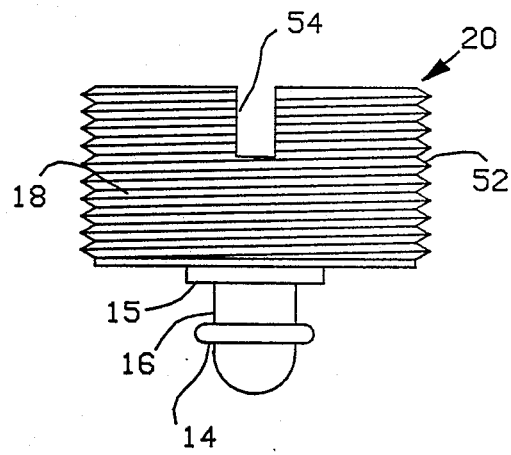
FIGS. 2a-c illustrate the various parts of the electrochemical half-cell of the screw-in ion selective electrode system of the present invention.
Figure 2C:
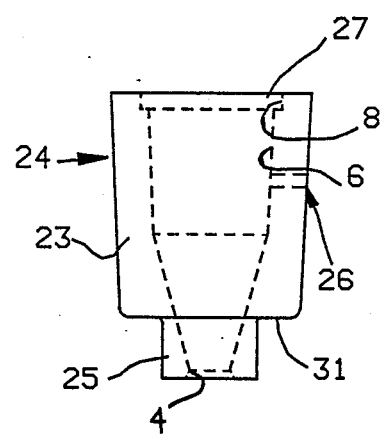
Figure 2A:
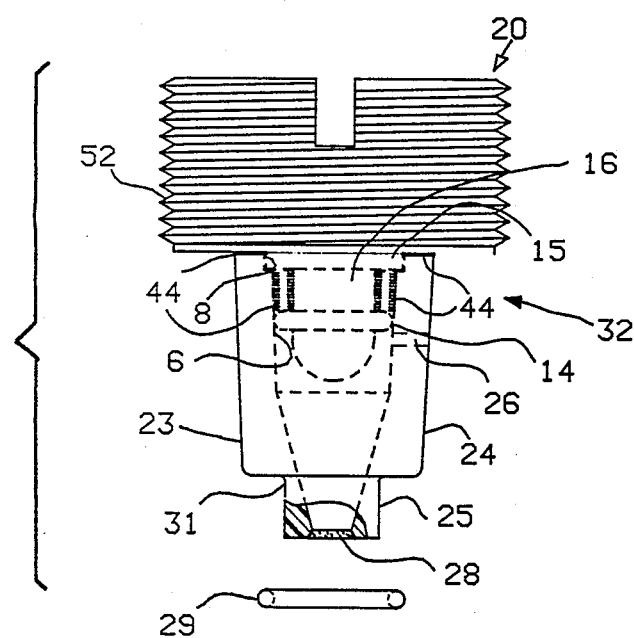

FIGS. 2a–2c illustrate the various parts of the electrochemical half-cell 32 of the screw-in ISE system of the present invention. Half-cell 32 includes an electrode 20 which is preferably formed of a solid silver core coated with a silver halide such as silver chloride. Electrode 20 (see FIG. 2b) has an upper section 18 of generally cylindrical shape with screw threads 52 formed around the exterior, and a lower section 16. The top part of the upper section 18 includes an indentation 54 for engaging a screw driver (not shown). Upper section 18 is preferably larger than lower section 16 and, in the presently preferred embodiment measures approximately 0.250 inch in diameter and approximately 0.124 inch in height. Lower section 16 is also generally cylindrical in shape but substantially hemispherical at the bottom. Axially spaced annular shoulders 14 and 15 extend around the outside cylindrical wall of lower section 16 and are positioned at opposite ends of lower section 16, with shoulder 15 being positioned at one end of lower section 16, thus, shoulder 15 coaxially abuts the bottom of upper section 18 as best shown in FIG. 2b.

Half-cell 32 further includes cup means 24 as shown in FIG. 2c. In general, the cup means 24 is sized to hold both lower section 16 of electrode 20 and a volume of fill solution not greater than about 200 micro-liters. Preferably the cup means 24 is sized to hold a volume of fill solution of from about 5 microliters to about 10 microliters. Cup means 24 is preferably molded from acrylic plastic and has an upper end 23 contiguous with a lower end 25. Upper end 23 has an outer wall substantially frusto-conical in shape. The interiors of upper end 23 and lower end 25 communicate in the form of an open area. Upper end 23 is in the general shape of a hollow cylinder with an open top 27 and measures approximately 0.187 inch in diameter and 0.146 inch in height. The wall of upper end 23 is preferably of varying thicknesses to form steps 8 and 6 on the interface as shown in FIG. 2c. As shown in FIG. 2a, the steps 8 and 6 conform to the outer diameters of shoulders 15 and 14 of the electrode's lower section 16 and facilitate sealing engagement between the lower section 16 and the upper end 23 of the cup means 24. An aperture 26 for introducing fill solution into cup means 24 is formed in the upper end 23, at a distance from the open top 27 of cup means 24 that preferably exceeds the distance between shoulder 15 shoulder 14.

Lower end 25 of cup means 24 is also generally a hollow cylinder and measures approximately 0.124 inch in diameter and 0.06 inch in height. There is an open internal space room upper end 23 to lower end 25. The inner wall of lower end 25 slopes inward in a funnel configuration. An orifice 4 is formed in a bottom portion of lower end 25 and is covered by membrane 28. The orifice 4 for the sensor half-cell is preferably circular, and measures approximately 0.025 inch in diameter.

As is known in the art, an ion sensitive membrane can be generally formed of a material containing polyvinyl chloride plus an ionophore. The ionophore forms the compound with the ion of interest. Suitable ionophores are well known for various ions such as potassium, sodium, calcium and chloride. For example, valinomycin is typically used for potassium. Other known ionophores can be used for other ions.

Prior to assembly of the half-cell 32, the electrode 20 is machined from a silver rod and then chloridized to form a Ag/AgCl compound. The membrane 28 is applied to cup means 24 by dispensing about 0.5 micro-liters of the appropriate membrane material over the orifice 4, and allowing the membrane 28 to dry or cure. An epoxy 44, is preferably applied to the electrode 20 in the area between shoulders 15 and 14, and also in the area defined by the intersection between upper section 18 and shoulder 15. The electrode 20 is then secured to the cup means 24 by engaging lower section 16 thereto, and clamping the half-cell 32 together until the epoxy 44 is cured. The epoxy should be cured with no voids or bubbles to prevent leakage of the fill solution 30, and should not extend into cup means 24 beyond shoulder 14.

FIG. 2a illustrates the assembled electrochemical half-cell 32 before introduction of the fill solution 30. The electrode 20 and cup means 24 are preferably aligned concentrically along the center-line of each as shown in FIG. 2a. Improper alignment may cause stress fractures in the cup means 24 when the electrode 20 is screwed into the test cartridge 12. The lower section 16 of the electrode 20 engages the upper end 23 of the cup means 24 such that the outer edges of shoulders 15 and 14 abut the steps 8 and 6, respectively in the inner wall of upper end 23. A silicone rubber o-ring 29 is sized to fit around the outer wall of lower end 25, and to abut the shoulder 31 formed by the intersection between upper end 23 and lower end 25. When in place, (see FIG. 4) the radial dimension of the o-ring 29 should not extend beyond the outer wall of upper end 23.

4. Reference Half-Cell

A variety of conventional reference electrode configurations may be utilized in conjunction with the present invention. One example of a conventional reference electrode contains an internal fill solution and a ceramic frit, as disclosed in U.S. Pat. No. 4,696,028, entitled Electrolyte Analyzer, granted on Mar. 10, 1987 to Kaltenbach et al. A preferred reference electrode is substantially the same as the screw-in configuration of the half-cell 32 as described herein, and has a porous membrane disposed across its orifice. Most preferred is a reference electrode substantially the same as half-cell 32 except for a cellulose acetate membrane separating the fill solution from the sample. Such a reference electrode and membrane composition is described in previously referenced U.S. Ser. No. 336,944 entitled Reference Electrode, filed concurrently herewith and assigned to the same assignee. The disclosure of that application is incorporated herein by reference.

5. Method of Manufacture

Figure 3A:
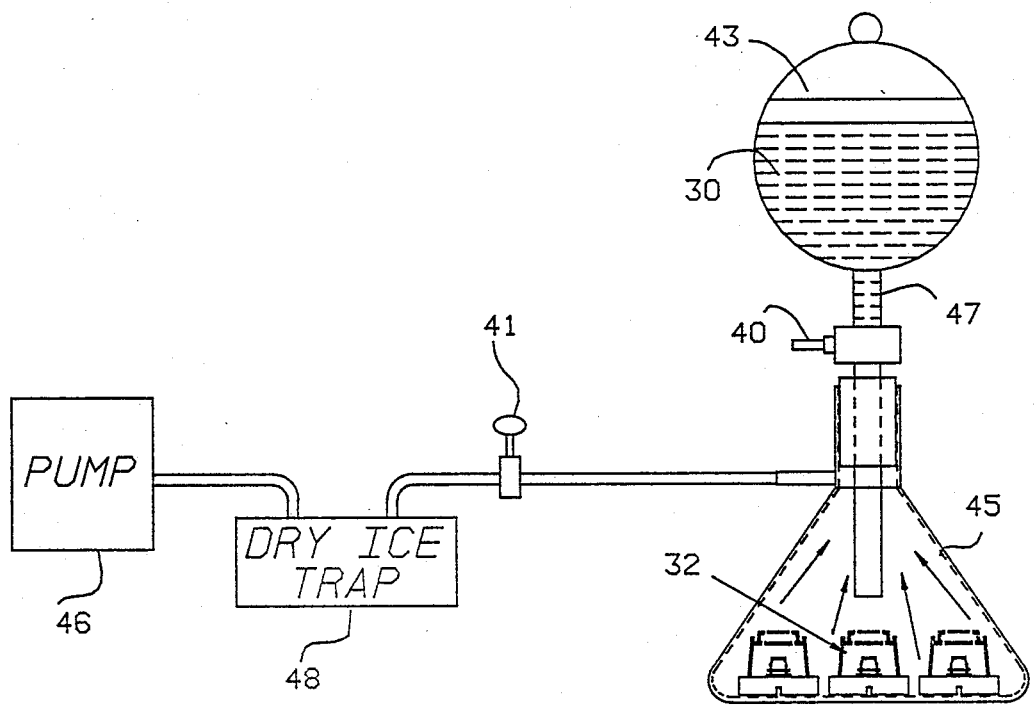
FIGS. 3a-b illustrate the vacuum method for introducing a fill solution into the cup section of a completely assembled electrochemical half-cell of the miniaturized screw-in ion selective electrode system.
Figure 3B:
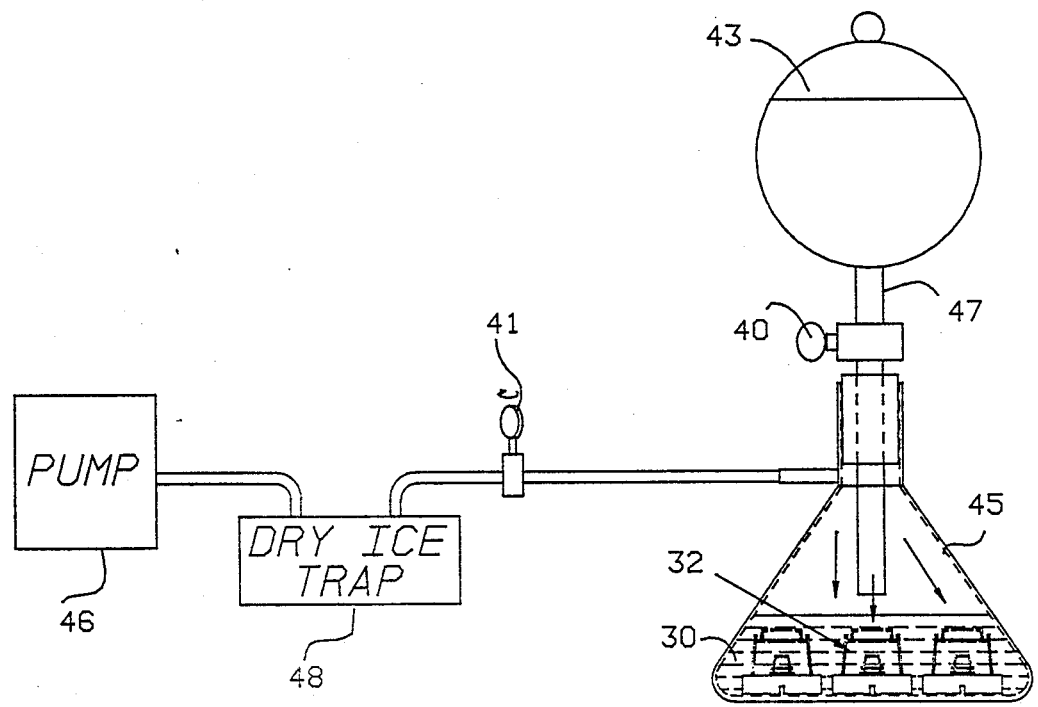

Referring now to FIGS. 3a–3b, a method for introducing the fill solution 30 into the half-cell 32 can be explained. Initially, one or more half-cells 32 are placed in a chamber 45 which can be evacuated via a pump 46 to create a substantial vacuum within the chamber 45. Fill solution 30 may be initially held in a vessel 43 which communicates with chamber 45 via a passage way 47. The passage way 47 is opened and closed by a first valve 40. For a human blood sample, the fill solution 30 comprises from about 1 to about 10 milli-Molor (mM) potassium chloride plus from about 50 to about 150 mM sodium chloride, dissolved in water. A preferred fill solution composition is comprised of about 7 mM potassium chloride plus about 100 mM sodium chloride, dissolved in water. Fill solutions can be tailored for other samples as is known by those skilled in the art. It is possible to include other excipients in the fill solution.

The pump vacuum is applied for approximately ten minutes. The fill solution 30 is then introduced into the vacuum environment of chamber 45 via first valve 40 until the half-cells 32 are completely covered by the fill solution 30. The fill solution 30 is allowed to finish degassing before the chamber 45 is slowly repressurized to one atmosphere by opening second valve 41. The fill solution 30 then enters the cup means 24 via the aperture 26. The chamber 45 is repressurized slowly to insure that there are no bubbles or voids in the fill solution 30, since the presence of air in the fill solution 30 can reduce the accuracy of the ISE's measurement. If the air bubble or void forms on the membrane surface, an electrical disconnect can result (i.e., no output from the ISE system). A dry ice trap 48 may be interposed between the pump 46 and the chamber 45 to keep vapor from reaching the pump 46. The half-cells 32 are then removed from the chamber 45 and any suitable means, such as a hot iron (not shown), is used to seal off the aperture 26. The same fill solution 30 is used for both the sensor and reference half-cells.

6. Use

In operation, the two portions of the test cartridge 12, the reusable portion 70 and the disposable portion 96, are snapped together with the two piercing pins 72 and 73 in the reusable portion 70 puncturing membranes in the disposable 96, thereby opening a passage for calibrators A and B to flow throughout both portions of test cartridge 12 according to a specified protocol. A blood sample is placed in the sample well 92 of the disposable portion 96. The test cartridge 12 is then inserted into the centrifuge head 10 of a centrifugal-type analyzer. The analyzer is started and the centrifuge head 10 attains a speed of approximately 1,800 rpm, or 500 times G, forcing the blood sample to flow into a blood separation chamber. If whole blood is being tested a short interval of time is allowed for blood separation; no such interval is necessary if a plasma or serum sample is used.

The two-dimensional centrifuge action of the analyzer operates to intermittently transfer the plasma or serum, calibrator A and calibrator B throughout the various passages and wells of the test cartridge 12, including flow passage 58. The particulars of this fluid transfer are fully described in previously referenced U.S. Ser. No. 337, 011 and will not be repeated in detail here. To summarize the operation, the two-dimensional centrifugal analyzer acts to sequentially bring first the calibrator A, then the sample, and then calibrator B into contact with the ISE system (reference and sensor half-cells 21 and 22) via flow passage 58. The ISE system generates a potential related to the ion concentration of the particular solution (calibrator A, sample, or calibrator B) present in flow passage 58 at the open intersection between flow passage 58 and the half-cells 21 and 22 disposed in the openings 56 and 57.

Calibrator A, the low end calibrator, preferably comprises about 4 mM potassium chloride, plus from about 20 to about 25 mM sodium acetate, plus about 100 mM sodium chloride, plus a preservative. Calibrator B, the high end calibrator, preferably comprises about 7 mM sodium chloride plus from about 20 to about 25 mM sodium acetate, plus about 100 mM sodium acetate, plus a dye and a preservative.

In the storage state when the reusable portion 70 is not in use, the reference and sensor half-cells 21 and 22 are in contact with a salt storage solution which is identical to calibrator B and which is present in the flow passage 58. The salt storage solution has an ionic strength similar to that of the sample of interest which in this particular application is blood. This allows minimum drift of the ISE system generated potential due to ionic strength changes when the sample contacts the half-cell 32. Also, both the reference and sensor half-cell fill solutions 30 are similar in formula to the salt soak solution in order to help provide a chemical equilibrium situation during storage.

As evident from the above description, the miniaturized screw-in ISE system of the present invention solves many of the problems associated with the measuring of electrolyte concentrations using a two-dimensional centrifugal analyzer and a multichamber test cartridge such as test cartridge 12. The small size and weight of each reference half-cell 32 and sensor half-cell 22 allows for operation of the ISE within the test cartridge 12, which is itself small and light-weight. The screw-in electrode 20 secures the half-cell 32 inside the test cartridge 12 and also provides a convenient point of electrical connection from the half-cell 32 to the read-out electronics of the test cartridge 12. The screw-in electrode 20 also provides for easy removal and replacement by the user with no special skill required. The electrochemical half-cell 32 is fully self-contained and needs only sample, calibrators, and read-out electronics. A salt storage solution having similar ionic strength as the sample, is kept in contact with each half-cell 32 during storage to help prevent drift of the ISE generated potential due to ion strength changes when the sample comes in contact with the half-cell 32. Also, both the reference and sensor fill solutions 30 are similar to the salt storage solution in order to help provide chemical equilibrium during storage. Finally, except for the composition of the membrane 28, the sensor 22 and the reference 21 half-cells are generally interchangeable for ease of manufacture, troubleshooting and repair.

While the above-described embodiment of the invention is preferred, those skilled in this art will recognize modifications of structure, arrangement, composition and the like which do not part from the true scope of the invention. All such modifications are intended to be covered by the appended claims.

We claim:

1. Apparatus for use in measuring an unknown concentration of an electrolyte in a sample comprising:
    a test cartridge having a flow passage adapted to pass a sample, and first socket means in communication with said passage;
    first cup means, adapted to hold a sensor fill solution of known ion concentration, having an open top and a bottom defining an orifice;
    a first electrode, secured to said first cup means at said top adapted to be in contact with said sensor fill solution and being further adapted to be removably mounted in said first socket means of said test cartridge, said first socket means also providing electrical contact between said test cartridge and said first electrode;
    a first membrane covering said first orifice, and disposed between said flow passage and said first cup means whereby contact of said sample with said first membrane creates a potential difference between said first electrode and said sample which is related to the unknown concentration of electrolyte in said sample.

2. The apparatus of claim 1 further comprising:
    a second socket means disposed in said test cartridge and in communication with said flow passage;
    a reference electrode disposed in said second socket means and in contact with said sample in said flow passage, said reference electrode being in a circuit with said first electrode.

3. The apparatus of claim 2 wherein said reference electrode has a threaded portion which is screwed into said second socket means, said second socket means providing electrical contact between said test cartridge and said reference electrode.

4. The apparatus of claim 3 therein said second socket means is formed of an electrically conductive material.

5. The apparatus of claim 4 wherein said electrically conductive material includes brass.

6. The apparatus of claim 2 wherein said reference electrode includes a silver core coated with a silver halide.

7. The apparatus defined in claim 2 wherein said reference electrode further comprises a second cup means holding a volume of a reference electrode fill solution, said volume being not greater than 200 micro-liters.

8. The apparatus defined in claim 2 further comprising:
    a reference electrode having fill solution;
    a salt storage solution flowing through said flow passage, said reference fill solution and said salt storage solution and said sample being substantially the same composition as said sensor fill solution.

9. The apparatus defined in claim 8 for a potassium determination wherein:
    said sensor fill solution comprises from about 1 to about 10 milli-molar solution of potassium chloride and from about 50 to about 150 milli-molar solution of sodium chloride dissolved in water.

10. The apparatus defined in claim 9 wherein said sensor fill solution comprises about 7 milli-molar solution of potassium chloride and about 100 milli-molar solution of sodium chloride dissolved in water.

11. The apparatus defined in claim 1 wherein said electrolyte is potassium.

12. The apparatus of claim 1 wherein said first electrode has a threaded portion which is screwed into said first socket means.

13. The apparatus of claim 1 wherein said first socket means is formed of an electrically conductive material.

14. The apparatus of claim 13 wherein said electrically conductive material includes brass.

15. The apparatus of claim 1 wherein said first electrode is formed of a silver core coated with a silver halide.

16. The apparatus of claim 1 wherein said first membrane is formed of an ion sensitive polymeric material.

17. The apparatus defined in claim 1 wherein said first cup means holds a volume of said sensor fill solution of not greater than 200 micro-liters.

* * * * *